(12) United States Patent
Tanaka et al.

(10) Patent No.: US 12,220,283 B2
(45) Date of Patent: Feb. 11, 2025

(54) ULTRASOUND IMAGING APPARATUS, SIGNAL PROCESSOR, AND SIGNAL PROCESSING METHOD

(71) Applicant: FUJIFILM Healthcare Corporation, Kashiwa (JP)

(72) Inventors: Chizue Tanaka, Chiba (JP); Misaki Maruyama, Chiba (JP); Teiichiro Ikeda, Chiba (JP); Kazuhiro Amino, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 373 days.

(21) Appl. No.: 17/846,928

(22) Filed: Jun. 22, 2022

(65) Prior Publication Data

US 2022/0409185 A1  Dec. 29, 2022

(30) Foreign Application Priority Data

Jun. 28, 2021 (JP) .................................. 2021-106840

(51) Int. Cl.
  *A61B 8/00* (2006.01)
  *G01S 7/53* (2006.01)
  (Continued)

(52) U.S. Cl.
  CPC ............ *A61B 8/585* (2013.01); *A61B 8/4488* (2013.01); *A61B 8/5207* (2013.01); *A61B 8/54* (2013.01);
  (Continued)

(58) Field of Classification Search
  CPC ....... A61B 8/5207; A61B 8/52; A61B 8/4488; A61B 8/585
  See application file for complete search history.

(56) References Cited

U.S. PATENT DOCUMENTS

2018/0235578 A1* 8/2018 Berger ................. A61B 8/5207
2018/0242951 A1* 8/2018 Hiroshima .......... G01S 7/52026

FOREIGN PATENT DOCUMENTS

JP  2007167116 A   7/2007
JP  2016-103839 A  6/2016
JP  2016-181869 A  10/2016

OTHER PUBLICATIONS

Japanese official action dated Dec. 12, 2023 (and English translation thereof) in connection with Japanese Patent Application No. 2021-106840.

* cited by examiner

*Primary Examiner* — Gerald Johnson
(74) *Attorney, Agent, or Firm* — Paul Teng

(57) ABSTRACT

Provided is an ultrasound imaging apparatus capable of reducing examination time with optimizing parameters on an examination basis. A subject is irradiated with an ultrasound wave, and a plurality of ultrasound transducers receives the ultrasound wave from the subject to obtain received signals. A feature value is calculated from the received signals, the feature value indicating a frequency-dependent characteristic of attenuation of the ultrasound wave, associated with propagation of the ultrasound wave through the subject. A predetermined processing is performed on the received signals using one or more received-signal processing parameters to generate an image. An image processing is performed on the generated image using one or more image processing parameters. Values of the received-signal processing parameter and the image processing parameter are determined based on the feature value.

14 Claims, 11 Drawing Sheets

(51) Int. Cl.
 *G01S 7/58* (2006.01)
 *G01S 15/89* (2006.01)
(52) U.S. Cl.
 CPC ................. *G01S 7/53* (2013.01); *G01S 7/58* (2013.01); *G01S 15/89* (2013.01)

ULTRASOUND IMAGING APPARATUS, SIGNAL PROCESSOR, AND SIGNAL PROCESSING METHOD

BACKGROUND OF THE INVENTION

Field of the Invention

The present invention relates to setting of imaging parameters for an ultrasound imaging apparatus.

Description of the Related Art

When performing medical ultrasonographic examination using an ultrasound imaging apparatus, an appropriate image for diagnosis can be obtained only after an examiner adjusts imaging parameters of an ultrasound probe or an imaging device, to proper values in relation to a patient and an imaging site. Since there is a large number of parameters to be adjusted, it takes time to set the imaging parameters and this increases complexity of the examination. For the purpose of shortening the examination time and reducing the complexity of the examination, there are known devices where imaging parameter sets are prepared in advance, and an appropriate parameter set is automatically selected according to the connected probe.

In addition, JP-A-2007-167116 (hereinafter, referred to as Patent Literature 1) discloses an apparatus for automatically selecting an appropriate imaging parameter set, based on weight, a body fat ratio, age, gender, body structure, and a diagnostic target site of the patient, which are registered in patient database in advance.

SUMMARY OF THE INVENTION

Technical Problem

The state of internal tissue and organs of an actual patient's body varies widely among patients. In addition, a way to press the probe against the patient is different depending on an examiner. Furthermore, even when examining the same organ, an appropriate image varies depending on details of the examination. Therefore, it is difficult to obtain an appropriate image for diagnosis, covering all the combinations of patients, examiners, and examination details, according to conventional techniques of automatic imaging setting. Eventually, there is required a work for manually setting the imaging parameters appropriately for each examination. This work for adjusting the parameters has to be carried out with considering the patient's condition, characteristics of ultrasound waves, and so on, and this requires knowledge and experience.

In addition, if the examiner is a beginner in performing medical ultrasound examination, manual adjustment of the imaging parameters of the device may be difficult in the first place. Furthermore, manually adjustable parameters may be limited to some of numerous parameters of the device, and there are also internally determined and non-variable parameters. Thus this causes limitations in obtaining an ultrasound image suitable for diagnosis.

Solution to Problem

An object of the present invention is to provide an ultrasound imaging apparatus capable of reducing the examination time, along with optimizing the parameters for each examination.

In order to achieve the object above, the ultrasound imaging apparatus of the present invention includes a receiver, a feature value detector, a signal-image processor, and a controller. The receiver receives signals outputted in time series from a plurality of ultrasound transducers that have received an ultrasound wave from a subject irradiated with the ultrasound wave. The feature value detector calculates from the received signals, a feature value indicating a frequency-dependent characteristic of attenuation of the ultrasound wave associated with propagation of the ultrasound wave through the subject. The signal-image processor executes a predetermined process using one or more received-signal processing parameters, in response to the received signals, thereby generating an image, and performs an image processing on the generated image, using one or more image processing parameters. The controller sets values of the received-signal processing parameters and the image processing parameters of the signal-image processor to execute the processing. The controller further includes a parameter determiner that determines a value or values of one or more parameters among the received-signal processing parameters and the image processing parameters, on the basis of the feature value calculated by the feature value detector.

According to the present invention, there is provided the ultrasound imaging apparatus that allows optimization of parameters in real time according to the state of the target for imaging, thereby generating an image having high diagnostic performance along with saving examination time.

DETAILED DESCRIPTION OF THE PREFERRED EMBODIMENTS

There will now be described embodiments of the present invention.

Sound waves have a characteristic of frequency-dependent attenuation in the course of propagation, and ultrasound signals received at each propagation distance, i.e. imaging depth (time), have different characteristics. In addition, depending on conditions of a patient and an imaging site, the frequency-dependent attenuation characteristic also varies according to the state of the medium (tissue) through which the sound wave propagates. Therefore, the characteristics of the received ultrasound signals are also various. Further, in transmission beam scanning, a region irradiated with the transmission beam may change, and thus the characteristics of the ultrasound signals change every moment.

The inventors of the present application have focused on those phenomena as described above, and analyzed the frequency-dependent attenuation characteristics of the time-series received signals outputted from the ultrasound transducers that have received the ultrasound wave, thereby comprehensively and conveniently figuring out the state of the tissue through which the ultrasound wave propagates. Then, according to a result of the analysis, there are provided values of parameters used for processing signals such as received signals. This allows reduction of examination time along with optimizing the parameters for each examination. Multiple parameters are prepared in advance, assuming the state of various subjects, and some parameters are selected therefrom, and this enables the processing based on the parameters, comprehensively and conveniently.

First Embodiment

Figure 1:
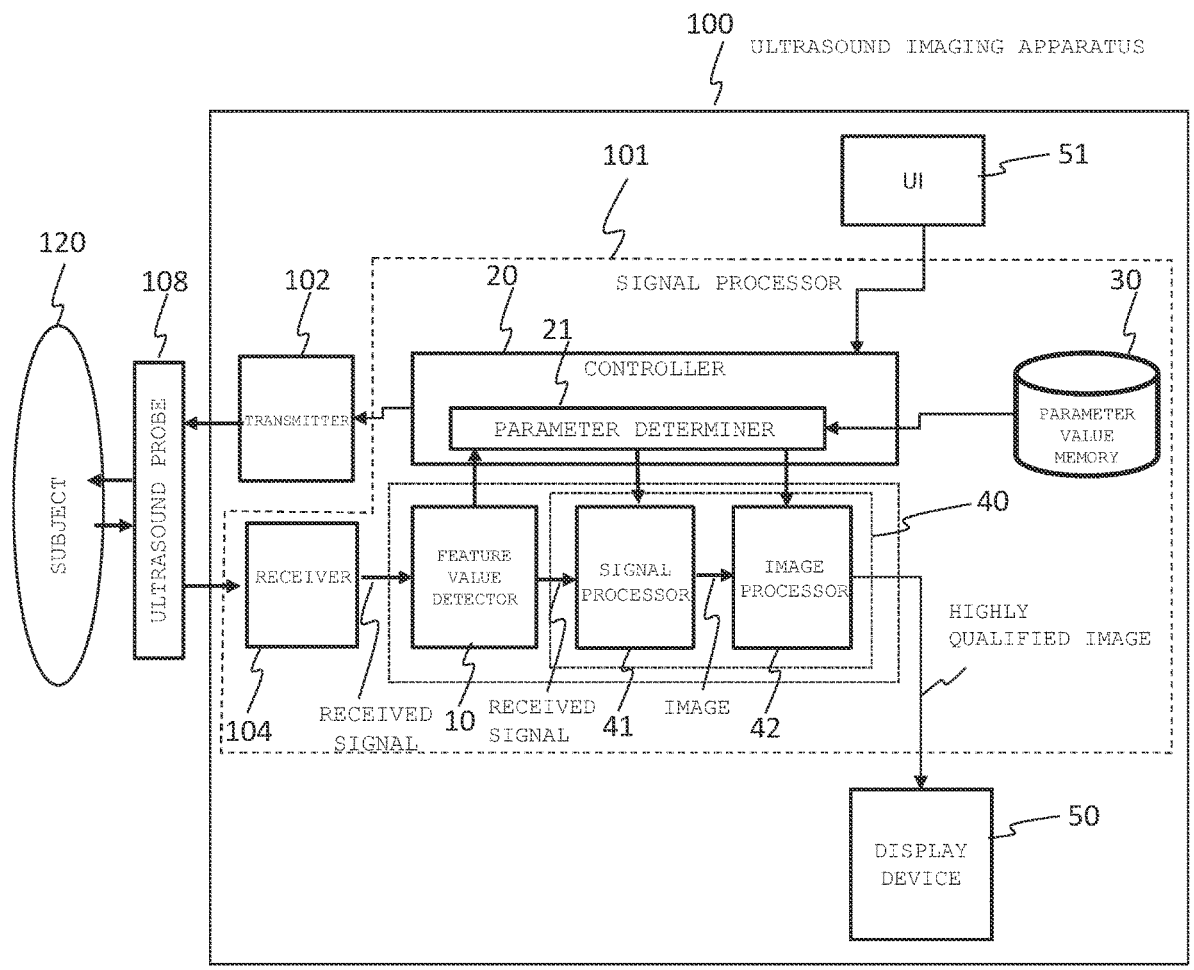
FIG. 1 is a block diagram showing an overall configuration of the ultrasound imaging apparatus 100 according to a first embodiment.

There will now be described the ultrasound imaging apparatus 100 of the first embodiment with reference to the accompanying drawings. FIG. 1 shows the overall configuration of the ultrasound imaging apparatus 100.

As shown in FIG. 1, the ultrasound imaging apparatus 100 includes a transmitter 102, a signal processor 101, a user interface (UI) 51 such as an input device, and a display device 50. The ultrasound imaging apparatus 100 is connected to an ultrasound probe 108 comprising an array in which a plurality of ultrasound transducers is arranged.

The transmitter 102 generates transmission signals and delivers the signals to a plurality of ultrasound transducers of the ultrasound probe 108. Then, the ultrasound transducers convert the transmission signals into an ultrasound wave, and the subject 120 is irradiated with the ultrasound wave. Here, there will be described an example where the ultrasound wave is transmitted in the depth direction of the subject 120.

The radiated ultrasound wave attenuates, for example, by partially reflected and scattered by objects within the subject 120, along with propagating in the subject 120. Frequency of the ultrasound wave being attenuated is different depending on the tissue constituting the subject 120 and factors within the tissue, such as the size of materials causing reflection and scattering. Therefore, the attenuation characteristics are different depending on the frequency of the ultrasound wave and the tissue constituting the subject 120. The reflected and scattered ultrasound wave propagates further, after changing the traveling direction, a portion of the ultrasound wave reaches the ultrasound transducers of the ultrasound probe 108, and then received. The time from when the subject 120 is irradiated with the ultrasound wave from the ultrasound transducers, reflected and scattered, and so on, until reaching the ultrasound transducers again and converted into received signals, depends on the depth of reflection, scattering, and the like. Further, the signal amplitude indicates reflection intensity, scattering intensity, and others, at the positions where reflection and scattering are performed within the subject 120.

Therefore, the received signals outputted in time series from a plurality of ultrasound transducers that have received the ultrasound wave being reflected, scattered, and the like, within the subject 120, include information of the depth and the intensity at positions where reflection, scattering, and others within the subject 120. With the use of such provided information, the signal processor 101 generates an image.

Furthermore, the received signals include information of frequency-dependent attenuation characteristics being different depending on the tissue constituting the subject 120 as described above. The signal processor 101 detects the frequency-dependent attenuation characteristics, and provides parameters used for processing the received signals and parameters used for processing an image being generated. This allows setting of parameters suitable for the state of the subject 120 and an imaging site. The processing in the signal processor 101 will be described specifically.

The signal processor 101 includes a receiver 104, a feature value detector 10, a signal-image processor 40, a controller 20, and a parameter value memory 30.

The receiver 104 receives the received signals from the multiple ultrasound transducers of the ultrasound probe 108, respectively, then performs signal sampling, and converts the received signals into digital signals. Thereafter, the receiver 104 performs processing such as adding the received signals from each ultrasound transducer after delaying the signals at a predetermined delay time, thereby performing receive-beamforming along a predetermined scan line. The receiver 104 performs the receive-beamforming for a plurality of scan lines, respectively, to generate received signals to which the receive-beamforming has been applied, with respect to each scan line.

The feature value detector 10 calculates a feature value indicating the frequency-dependent characteristic of ultrasound-wave attenuation occurring with propagation of the ultrasound wave in the subject, based on the received signals for each transducer or based on the received signals after receive-beamforming on a specific scan line.

The signal-image processor 40 executes a predetermined processing on the signals after receive-beamforming, using one or more received signal-processing parameters, and generates an image. Thereafter, the signal-image processor performs image processing on thus generated image using one or more image processing parameters.

The controller 20 sets one or more values among the received-signal processing parameters and the image processing parameters, to be used by the signal-image processor 40 for processing, and allows the signal-image processor 40 to execute the processing. The controller 20 includes a parameter determiner 21 that receives the feature value calculated by the feature value detector 10, and determines the value of one or more parameters among the received-signal processing parameters and the image processing parameters, based on the feature value.

Figure 2:
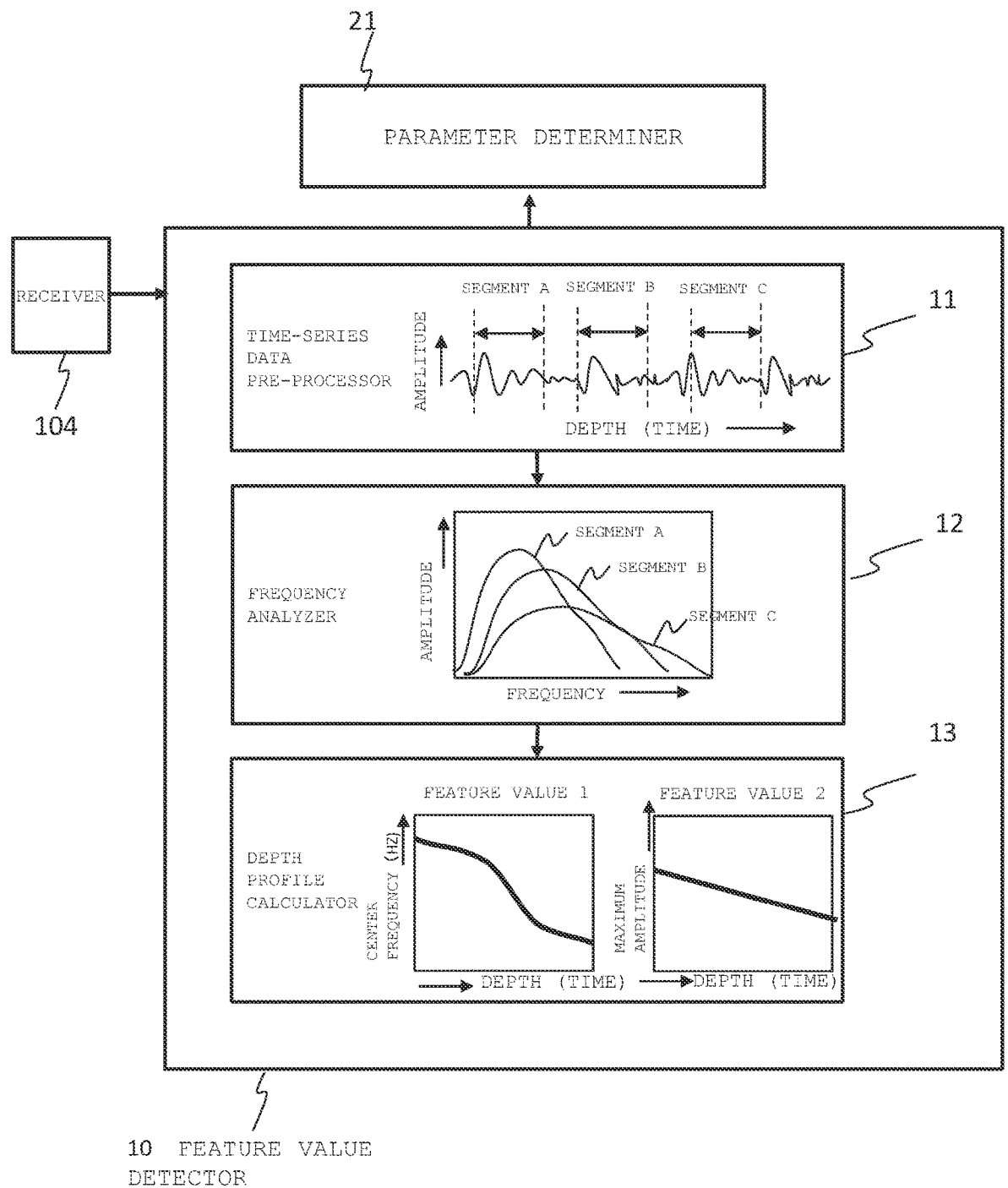
FIG. 2 is a block diagram showing a configuration of the feature value detector 10 according to the first embodiment.

With reference to FIG. 2, a configuration of the feature value detector 10 will be described. Hereinafter, there will be described an example where the feature value detector 10 calculates the feature value by processing the received signals after receive-beamforming. The feature value may also be calculated based on the received signals for each ultrasound transducer before the receive-beamforming is applied.

The feature value detector 10 includes a time-series data pre-processor 11, a frequency analyzer 12, and a depth profile calculator 13.

The time-series data pre-processor 11 receives the received signals from the receiver 104 after the beamforming is applied along a predetermined scan line, extracts signals within a predetermined depth (time) range, and performs processing such as noise reduction.

The time-series data pre-processor 11 divides the received signals, by a predetermined interval and width in the depth (time) direction, and sets a plurality of depth segments (for example, depth segments A, B, and C).

The frequency analyzer 12 performs processing such as Fourier transform on the received signals in each of the depth segments (A, B, and C), and calculates information of the frequency components that vary in the depth direction.

According to the information of the frequency components that changes in the depth direction, being obtained by the frequency analyzer 12, the depth profile calculator 13 obtains the change in the depth direction of the characteristics indicated by a predetermined frequency component, and outputs the result as the feature value. For example, there are calculated changes as the feature values, including the change in the depth (time) direction of the center frequency of the received signals, the change in the depth (time) direction of the transmission band of the received signals, the change in the depth (time) direction of the maximum amplitude within a predefined frequency section, and the change in either of power and energy in the depth (time) direction. In the example of FIG. 2, the depth profile calculator 13 calculates as the feature value 1, the change in the depth direction of the center frequency of the received signals, and calculates as the feature value 2, the change in the depth direction of the maximum amplitude within the frequency section from the frequency f1 (e.g., 1.5 MHz) to the frequency f2 (e.g., 5.5 MHz).

Figure 3:
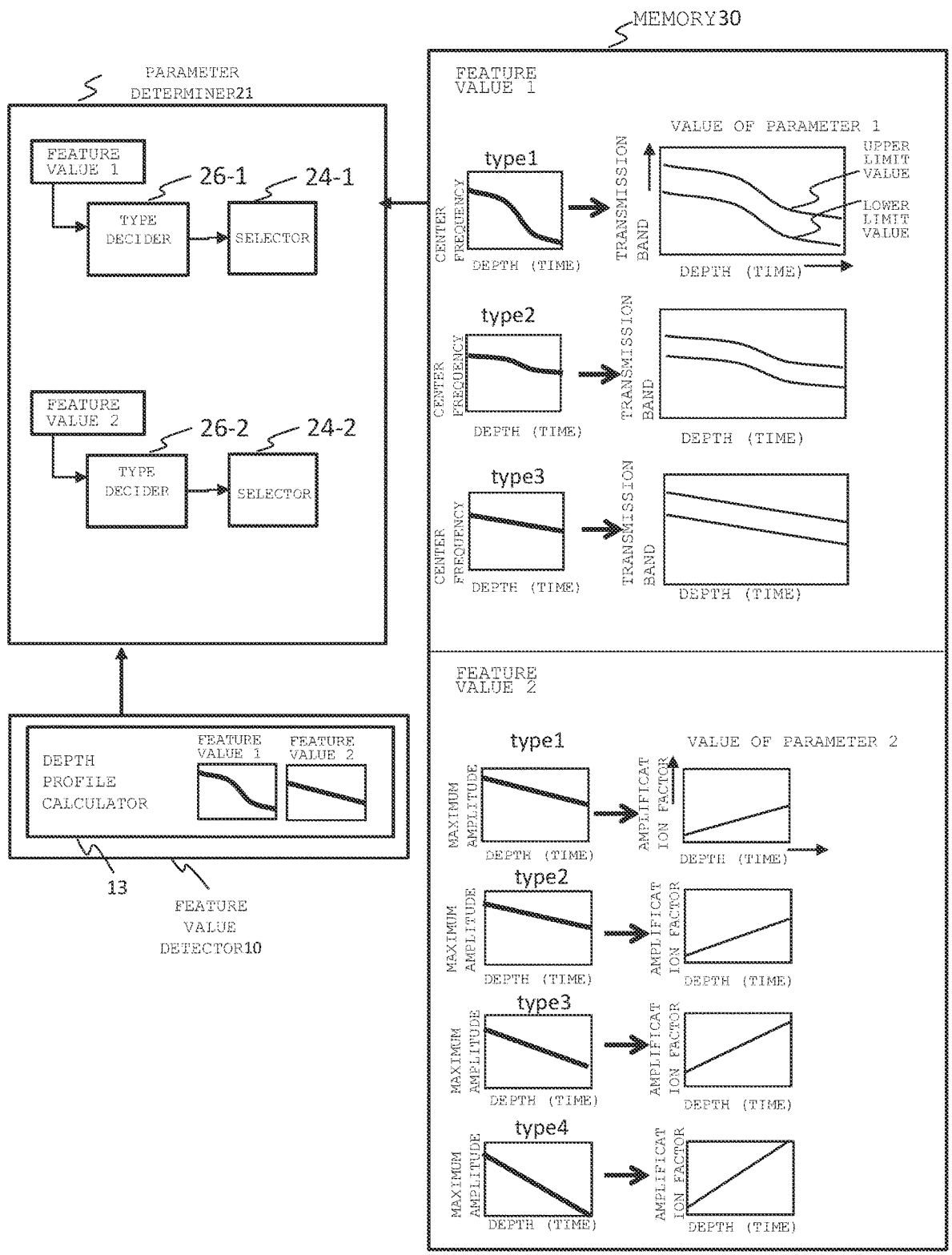
FIG. 3 is a block diagram showing a configuration of the parameter determiner 21 and the parameter value memory 30 according to the first embodiment.

With reference to FIG. 3, there will be described the configurations of the parameter determiner 21 and the parameter value memory 30. As one of the received-signal processing parameters, for example, there is a parameter to change one or more values of a depth-varying bandpass filter, a depth-varying receive aperture, and a depth-varying sound speed, to process the received signals. Further, a time gain control is one of the image processing parameters.

Multiple types of the feature values calculated by the depth profile calculator 13 are provided in advance in the parameter value memory 30, each type having a different way of change in the depth direction, and the multiple types are stored for each feature value. For example, as shown in FIG. 3, the feature value 1 (center-frequency change in the depth direction of the received signals) is provided with types 1 to 3 each having different change amount (slope or presence/absence of step) of the center frequency in the depth direction. The feature value 2 (change of the maximum amplitude in the depth direction within the segment from frequency f1 to frequency f2) is provided with types 1 to 4 each having different change amount of the maximum amplitude (slope).

In the parameter value memory 30, there are stored predetermined values of the received-signal processing parameter or of the image processing parameter in association with each of the multiple types of feature values 1 and 2.

For example, in the example shown in FIG. 3, the types 1 to 3 of the feature value 1 (center frequency change in the depth direction of the received signals) are respectively associated with the values of the parameter 1 being the received-signal processing parameter for changing the transmission band of the depth-varying bandpass filter in the depth direction. Specifically, in the example of FIG. 3, respectively for the types 1, 2, and 3 of the feature value 1, there are predetermined values of the parameter 1 for changing the frequency of the upper limit value and the lower limit value of the −6 dB transmission band of the depth-varying bandpass filter in the depth direction. The values of the parameter 1 are stored in the parameter value memory 30 in association with the types 1, 2, and 3, respectively.

There are predetermined values of the parameter 2 being the image processing parameter to change the amplification factor of the time gain control in the depth (time) direction, respectively associated with types 1 to 4 of the feature value 2 (the maximum amplitude within the segment from frequency f1 to frequency f2). The values of the parameter 2 are stored in the parameter value memory 30, in association with the types 1 to 4, respectively.

More specifically, the parameter values in the parameter value memory 30 are associated respectively with the types of the depth profile (change in the time direction) of the feature value, as shown in FIG. 3. For example, three types are provided for the feature value 1 (center frequency change of received signals in the depth direction) with the change of depth; type 1 in which the center frequency decreases stepwise, type 2 in which the frequency decreases smoothly, and type 3 in which the frequency decreases with a constant slope. Different values of parameter 1 (depth change in the transmission band of the depth-varying bandpass filter) are assigned to the types 1 to 3, respectively. In addition, the feature value 2 (maximum amplitude within the segment from frequency f1 to frequency f2) is provided with types 1 to 4 having different inclination amounts of attenuation in the depth direction, and the values of the parameter 2 having different inclination amounts are assigned respectively to types 1 to 4, that increase the amplification factor of the time gain control in the depth direction.

As shown in FIG. 3, the parameter determiner 21 is provided with type deciders 26-1, 26-2, and so on, and selectors 24-1, 24-2 and so on, respectively for varieties of the feature value. The type deciders, including 26-1 and 26-2, determine which of the types of feature value stored in the parameter value memory 30 corresponds to the feature value detected by the feature value detector 10. The selectors, including 24-1 and 24-2, select a value of the parameter corresponding to the determined type, thereby determining the value of the parameter appropriate for processing the received signals from which the feature value is extracted.

Specifically, the type deciders 26-1 and 26-2 compare the depth profile of the feature value, with the multiple types of the depth profile of the feature values stored in advance in the parameter value memory 30 to determine the most suitable type. As a method of determining the type according to the type deciders such as 26-1 and 26-2, there is employed a method of analytically selecting the type having a high degree of coincidence between the depth profile of the feature value received from the feature value detector 10, and curves of the depth transition of the multiple feature value types. It is also possible to employ a method for selection, for example, where the selection is performed according to programs that implement a deciding method following a preset type categorizing rule. It is also possible to employ as the type decider, a learning model made by machine learning using a learning dataset in which depth profiles of the feature value are set as input data and a corresponding type is set as correct answer data.

Further, the signal processor 101 of the present embodiment has a configuration that the processing of the feature value detector 10 and the processing of the signal-image processor 40 are performed according to pipeline processing. In addition, the processing by the feature value detector 10 is performed before the signal-image processor 40. With this configuration, the parameter determiner 21 obtains a parameter value from the feature value detected by the feature value detector 10 for a certain received signal. Then, the controller 20 sets thus obtained value as a parameter value used in the signal-image processor on the subsequent stage, and this parameter value can be used for processing that received signal.

Thus, the controller 20 can reflect the feature value of the received signal in real time on generation of an image according to the signal-image processor 40. Therefore, the signal-image processor 40 is allowed to generate the image appropriate for diagnosis, using the parameter suitable for the state of a portion of the subject 120 from which the received signal is obtained.

Specifically, as shown in FIG. 1, the signal-image processor 40 includes a signal processor 41 that performs processing on the received signals to generate an image, and an image processor 42 that performs processing on the generated image. The controller 20 delivers control signals to the feature value detector 10, the signal processor 41, and the image processor 42, respectively, and executes the pipeline processing to perform processing in parallel. Thus, the controller 20 instructs the feature value detector 10 to detect the feature value, then receives the feature value, and the parameter determiner 21 determines the received-signal processing parameter and the image processing parameter, in association with the feature value. Then, the controller 20 delivers to the signal processor 41, the received-signal processing parameter and the control signal to perform the signal processing, at a timing when the received signal is passed from the feature value detector 10 to the signal processor 41. Further, the controller 20 delivers to the image processor 42, the image processing parameter and the control signal for performing the image processing, at a timing when the image generated by the signal processor 41 is passed to the image processor 42.

Next, with reference to the flowchart of FIG. 4, there will be described an operation of each part of the signal processor 101. In this example here, the signal processor 101 can be configured by hardware. For example, a circuit may be designed using a custom IC such as ASIC (Application Specific Integrated Circuit) and a programmable IC such as FPGA (Field-Programmable Gate Array) to implement the functions of each part. It is also possible to implement the functions of a part and all of the signal processor 101 by software. In that case, a computer, or the like, including a processor such as a CPU (Central Processing Unit) and a GPU (Graphics Processing Unit) and a memory, may constitute a part or all of the signal processor 101, and the CPU reads and executes the programs stored in the memory, thereby implementing the functions.

The transmitter 102 delivers transmission signals to the multiple ultrasound transducers of the ultrasound probe 108, and the ultrasound probe 108 transmits an ultrasound wave to the subject 120. While a portion of the ultrasound wave is reflected and scattered in the subject 120, the ultrasound wave propagates in the subject 120, and then the ultrasound wave is subjected to frequency-dependent attenuation. The reflected and scattered ultrasound wave reaches the ultrasound transducers, and converted into received signals. Then, the ultrasound transducers output received signals in time series.

(Step S501)
The receiver 104 receives the time-series received signals from the ultrasound transducers, and performs receive-beamforming along a predetermined scan line.

(Step S502)
The time-series data pre-processor 11 extracts a predetermined depth (time) range of the received signal data after receive-beamforming, and sets a plurality of depth segments (e.g., segments A, B, and C) in a predetermined interval and width.

(Step S503) The frequency analyzer 12 performs frequency analysis on the received signals in each of the segments (A, B, and C), and obtains frequency component information that varies for each depth segment (for each depth).

(Step S504)
The depth profile calculator 13 calculates one or more feature values being predetermined, based on the frequency component information that varies for each depth segment (for each depth). Here, the feature value detector 10 calculates as the feature value 1, center frequency change in the depth (time) direction of the received signals, and calculates as the feature value 2, a maximum amplitude of the frequency section from a predetermined frequency A to frequency B (see FIG. 2).

(Step S505)
The type deciders 26-1 and 26-2 of the parameter determiner 21 receive the feature value 1 and the feature value 2 from the feature value detector 10, and determine which of the predetermined types corresponds to each of the feature values (feature value 1 and feature value 2).

Figure 4:
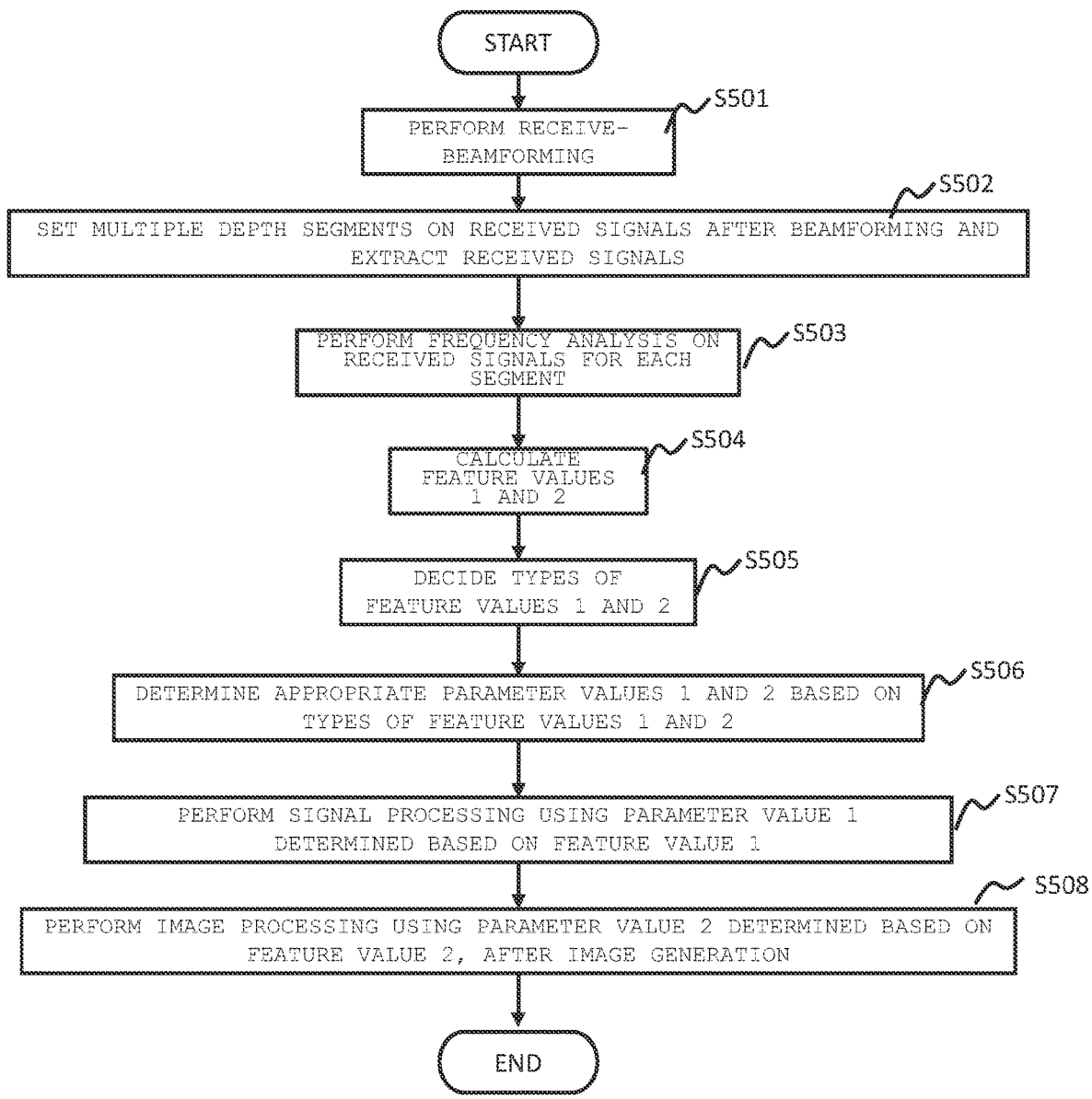
FIG. 4 is a flowchart showing an operation of each part in a signal processor 101 according to the first embodiment.

(Step S506)
The selectors 24-1 and 24-2 read from the parameter value memory 30, values of the parameter corresponding to the determined type, for each of the feature values (feature value 1 and feature value 2), and determine the value of the parameter corresponding to the feature value (see FIG. 4). The processing above is performed for all the feature values 1 and 2. Accordingly, for example, it is possible to determine from the feature value 1, a value of the parameter 1 for changing the transmission band of the depth-varying bandpass filter in the depth (time) direction. From the feature value 2, a value of the parameter 2 is determined, which changes the amplification factor of the time gain control in the depth (time) direction.

The controller 20 sets to the signal processor 41, among the parameters determined by the parameter determiner 21, a value of the parameter for the received-signal processing, determined based on the type of the feature value 1 (change of the transmission band of the depth-varying bandpass filter in the depth direction). The controller 20 further sets to the image processor 42, a value of the parameter for image processing determined based on the type of the feature value 2 (change of the amplification factor of the time gain control in the depth direction). As for the values of parameters necessary for the received-signal processing, other than the parameters 1 and 2, the controller 20 sets predetermined values or values provided by an operator.

(Step S507)
The signal processor 41 uses the parameter 1 (the transmission band of the depth-varying bandpass filter) provided in step S506 to perform a filtering process for transmitting the received signals after receive-beamforming, only in the frequency band that is set for each depth. Thus processed received signals are delivered to the image processor 42. It is also possible that in the depth-varying bandpass filter processing, the feature value 1 is calculated for the received signals of each scan line to determine the parameter 1, and the received signals are processed using thus determined parameter 1. It is further possible that in the depth-varying bandpass filtering, the feature value 1 is determined for the received signals of one scan line, and using this parameter 1, the same depth-varying bandpass filtering is performed on the received signals of all the scan lines that are used to generate a frame.
(Step S508)

The image processor 42 arranges the signals after receive-beamforming, received for each scan line, and generates an image of one frame. The image processor 42 uses the image processing parameter 2 (change in the depth direction of the amplification factor of the time gain control) that is provided in step S506 to perform the image processing on the generated image. Specifically, the image processor 42 uses the amplification factor of the time gain control provided as the parameter 2 to perform processing on the generated image.

When the parameter determiner 21 has not yet determined the image processing parameter from the feature value, the controller 20 outputs only a control signal to allow the image processor 42 to generate an image. The image processor 42 arranges the received signals after receive-beamforming for each scan line, generates an image of one frame, and then, and performs image processing using the determined value of the parameter.

In any of the cases above, the image processor 42 delivers the generated image to display the image on the display device 50.

According to the present embodiment, the time-series received signal data on which the information in the depth direction of the subject 120 is reflected, is used to obtain the depth profile of the feature values, thereby figuring out the state of the received signals comprehensively and conveniently. Therefore, by using the depth profiles of the feature values, it is possible to determine the parameter values corresponding to the characteristics of the patient and the imaging site.

Further, since the ultrasound imaging apparatus of the present embodiment is implemented according to the pipeline processing of multiple processes, it is possible to obtain from the received signals in the upstream, the most suitable values as the parameters requiring optimization, allowing simultaneous optimization of the downstream processing. This enables the ultrasound imaging apparatus to provide diagnostic images using optimal imaging parameters for each frame. The parameters are optimized in real time according to the state of the imaging target, whereby it is possible to provide an image with high diagnostic performance with saving the examination time.

The transmitter 102 may have the configuration where transmission signals are generated on the basis of one or more parameters. In this case, the parameter determiner 21 of the controller 20 may determine the value of the parameter of the transmitter 102 based on the depth profile of the feature value calculated by the feature value detector 10.

Second Embodiment

Figure 5:
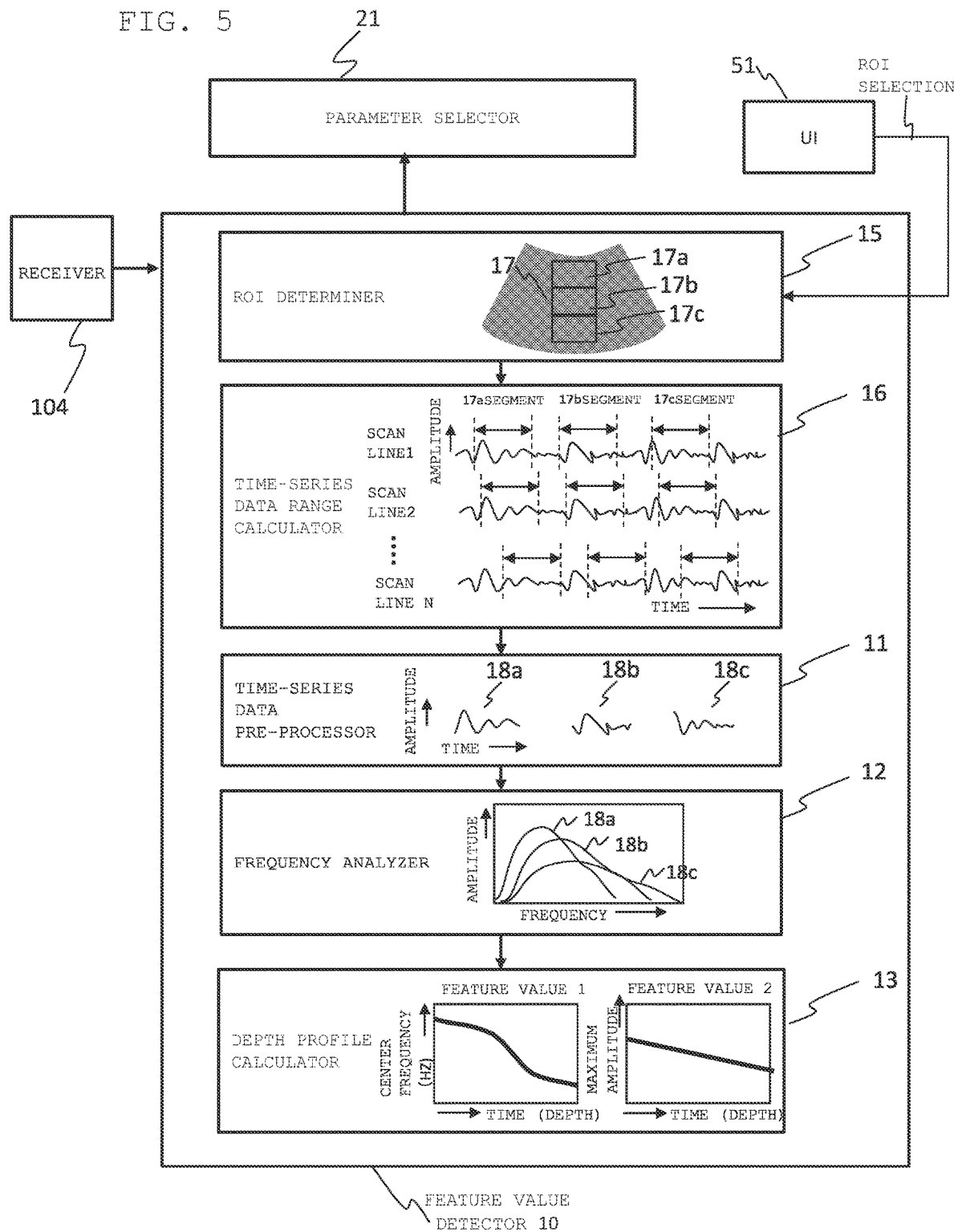
FIG. 5 is a block diagram showing the configuration of the signal processor 101 according to a second embodiment.
Figure 6:
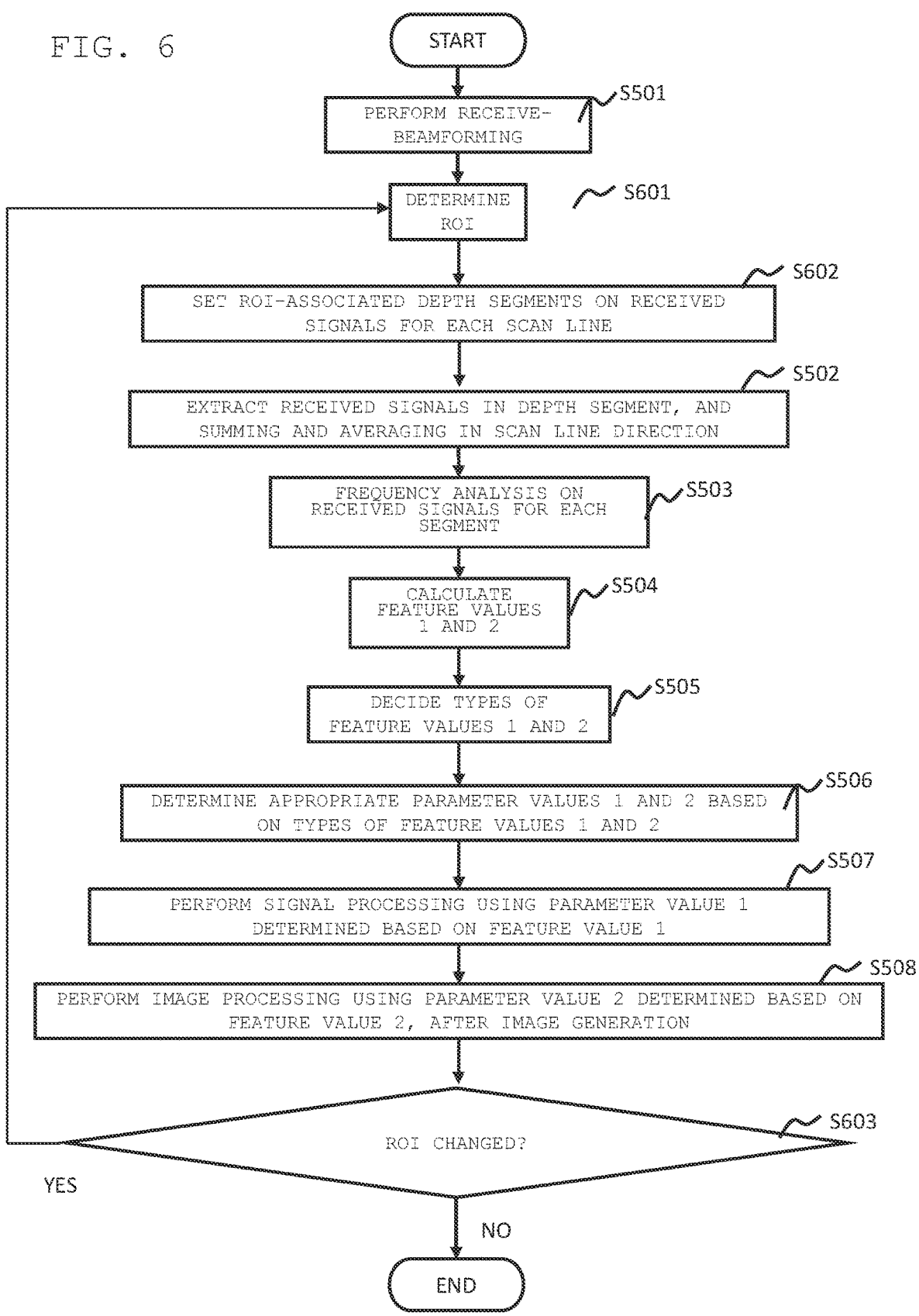
FIG. 6 is a flowchart showing the operation of the signal processor 101 according to the second embodiment.

With reference to FIGS. 5 and 6, there will be described the ultrasound imaging apparatus according to the second embodiment of the present invention. FIG. 5 illustrates the configuration of the signal processor 101, mainly the feature value detector 10, and FIG. 6 shows a flowchart illustrating the operation of the signal processor 101.

The ultrasound imaging apparatus of the second embodiment has the same configuration as the first embodiment, but differs from the first embodiment in that an ROI (Region of Interest) is provided, and the depth profile of the feature value is calculated from the received signals after receive-beamforming, the received signals being used for generating an image within the ROI. By setting the ROI in the area where patient characteristics are shown, it is possible to set the parameter value suitable for the area showing the patient characteristics. The ultrasound imaging apparatus of the present embodiment will be described in the following, focusing on the points different from the first embodiment.

As shown in FIG. 5, the feature value detector 10 includes an ROI determiner 15 and a time-series data range calculator 16, in addition to the configuration of the feature value detector 10 of the first embodiment. The ROI determiner 15 determines an ROI 17 for detecting the feature value based on the information received from the user. The time-series data range calculator 16 sets depth segments on the received signals after receive-beamforming for each scan line by using the determined ROI 17.

With reference to FIG. 6, there will now be described the operation of the ultrasound imaging apparatus of the second embodiment. In the flowchart of FIG. 6, steps S601 and S602 are added between step S501 and step S502 in the flowchart of FIG. 4, and step S603 is added after step S508. There will now be described the steps which are different from FIG. 4.
(Step S501)

The receiver 104 receives the time-series signals from the ultrasound transducers, and performs the receive-beamforming along a predetermined scan line.
(Step S601)

The ROI determiner 15 determines the ROI 17 for detecting the feature values, in an area selected by the user through the UI 51 and the controller 20. For example, the user may select a representative area (a particular depth and size) where the subject's characteristics are shown, to automatically determine an imaging area from the shallowest to the deepest area, including thus selected area, and then the ROI 17 is determined. Also, within the ROI 17, there are determined small ROIs (ROIs 17a to 17c in the example of FIG. 5) with appropriate depth-width for detecting the feature values. The representative area may indicate a predetermined position (e.g., the center of the image) and its size.
(Step S602)

The time-series data range calculator 16 extracts the received signals of N scan lines included in the lateral direction (the azimuth direction) of the respective ROIs 17a to 17c determined by the ROI determiner 15, and sets the depth segments in each depth range, corresponding to each of the depth ranges of the respective ROI 17a to 17c of the received signals of multiple scan lines. That is, the ranges in the depth direction (longitudinal direction) of the ROIs 17a to 17c are reflected on the depth segments of the time-series data, and the range in the lateral direction (azimuth direction) of the ROI is reflected on the number of scanning lines.
(Step S502)

The time-series data pre-processor 11 extracts signals in the multiple depth segments in association with the ROIs 17a to 17c, respectively set to the received signals in the N scan lines in step S602. Further, the time-series data pre-processor 11 averages and sums in the scan line direction, the received signals in the depth segments corresponding to the ROI 17a to 17c of the received signals in N scan lines. That is, the received signals extracted for the same depth segment of the ROI 17a from the received signals of the N scan lines are averaged and summed, and this allows noise reduction. This processing is also performed for each of the ROIs 17b and 17c. The received signals after the summing-averaging process (the signals 18a, 18b, and 18c in the example of FIG. 5) are transmitted to the frequency analyzer 12.

(Steps S503 to S506)

In steps S503 to S506, similar to the first embodiment, the frequency analyzer 12 performs the frequency analysis on the received signals after the summing-averaging for each depth segment, the feature value detector 10 calculates the feature values 1 and 2, and the parameter determiner 21 determines the parameters 1 and 2.

(Steps S507 to S508)

In steps S503 to S506, the signal processing and the image processing are performed using the determined values of parameters 1 and 2, for not only the received signals corresponding to the ROI 17 but also the received signals of the entire image, and then an image is generated. The controller 20 displays the generated image on the display device 50.

(Step S603)

The controller 20 shows a screen on the display device 50, to the user viewing the generated image, for prompting the user as to whether the position or the size of the ROI 17 should be changed. When the user chooses to change the ROI 17 via the UI 51, the process returns to the step S602, and then the position and/or the size of the ROI 17 is changed. Then, steps S502 to S508 are executed again based on the ROI 17 after the change.

According to the ultrasound imaging apparatus of the second embodiment, only the received signals in the ROI 17 provided in a representative area showing the patient characteristics are used for detecting the feature values, among the received signals of the entire scanning range, thereby enabling detection of data with stable feature values, and this allows stable determination of the parameter values.

Third Embodiment

Figure 7:
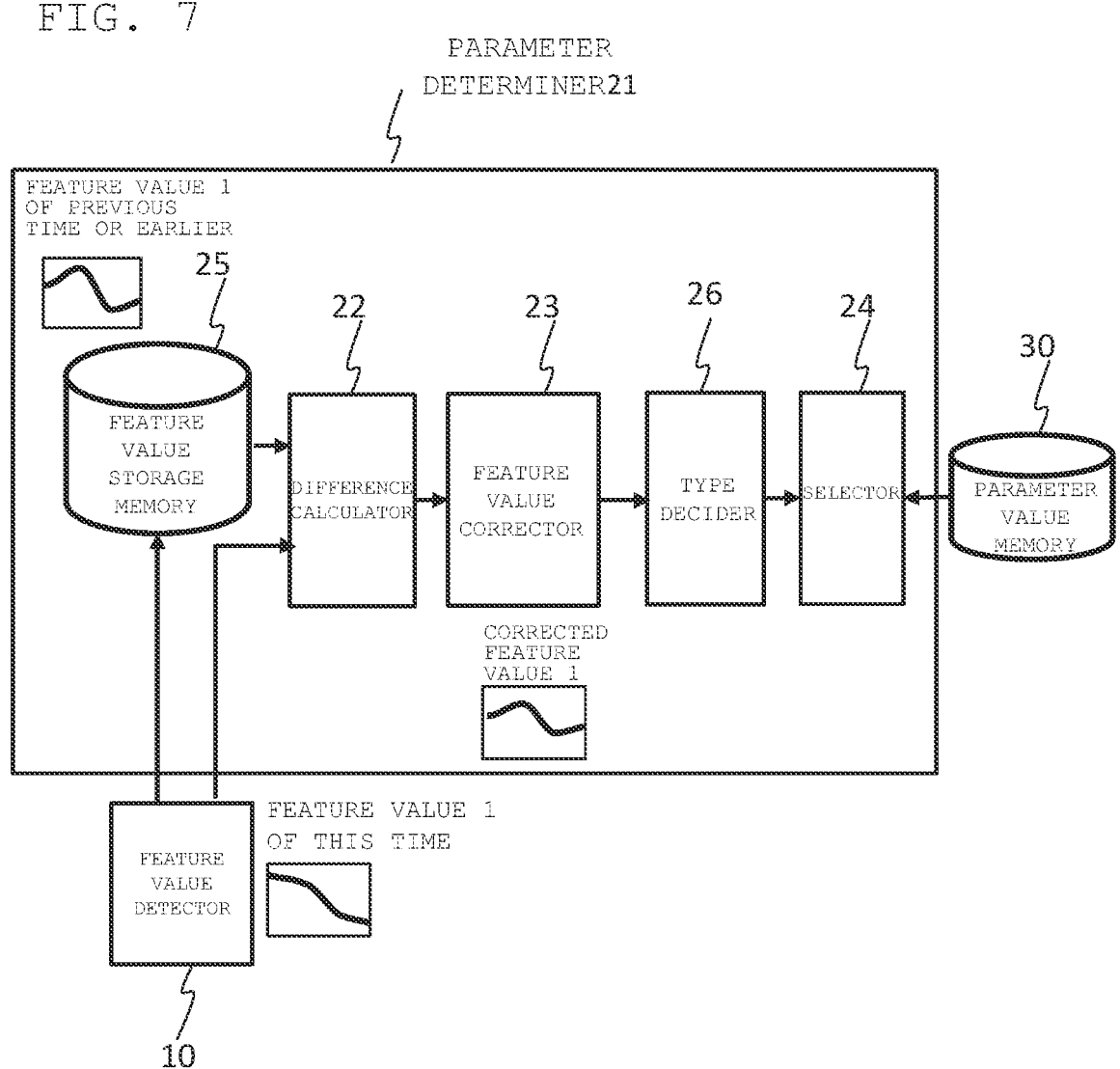
FIG. 7 is a block diagram showing the configuration of the parameter determiner 21 according to a third embodiment.
Figure 8:
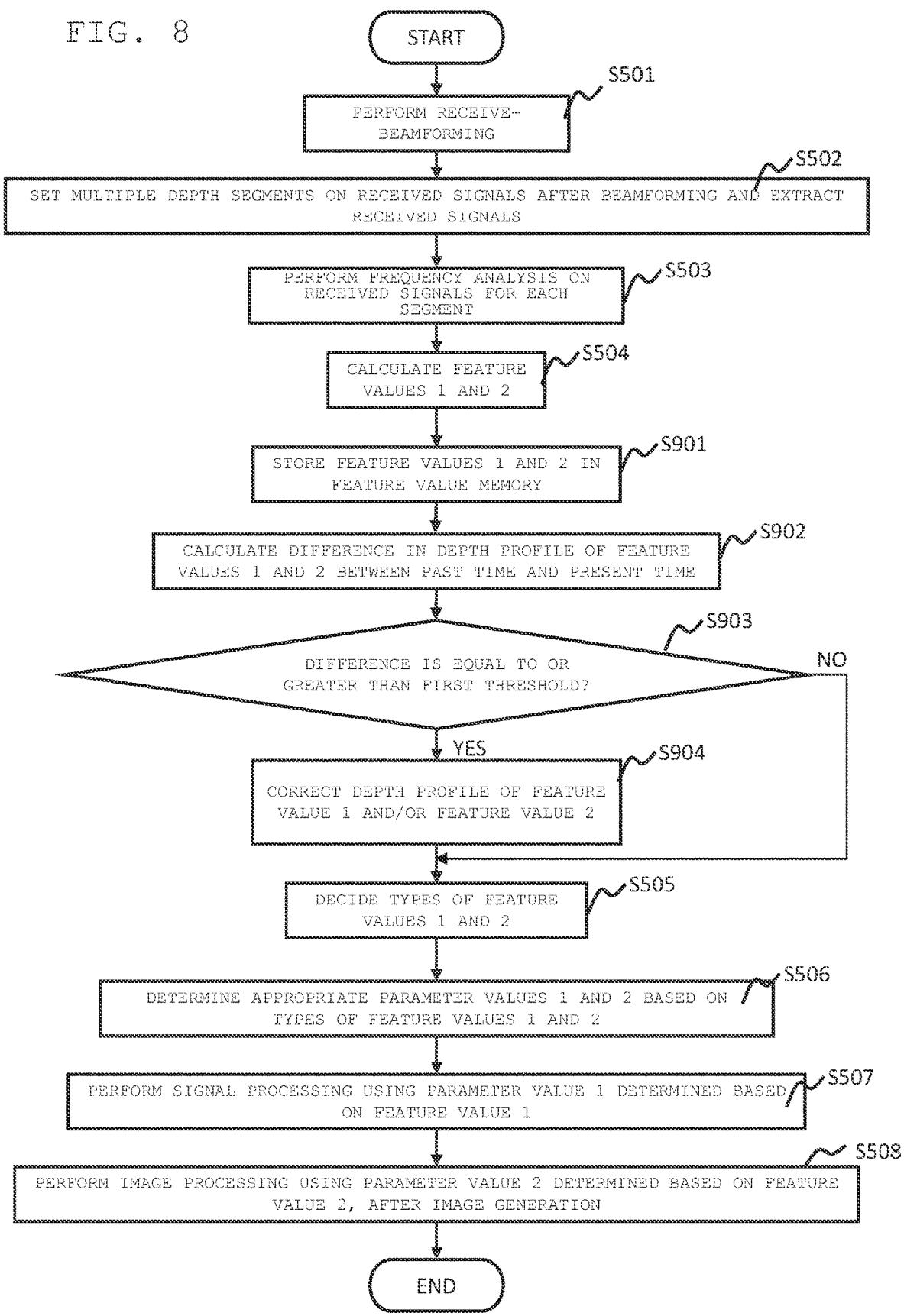
FIG. 8 is a flowchart showing the operation of the signal processor 101 according to the third embodiment.

With reference to FIGS. 7 and 8, the ultrasound imaging apparatus of the third embodiment of the present invention will be described. FIG. 7 illustrates a configuration of the parameter determiner 21 of the third embodiment, and FIG. 8 is a flowchart showing the operation of the signal processor 101.

The ultrasound imaging apparatus of the third embodiment has the same configuration as the first embodiment, but the parameter determiner 21 includes a feature value storage memory 25, a difference calculator 22, a feature value corrector 23, a type decider 26, and a selector 24. The feature value storage memory 25 stores depth profiles of the past feature values. The difference calculator 22 compares the depth profiles of the current and past feature values to calculate a difference therebetween. When the difference is large, the feature value corrector 23 corrects the depth profile of the current feature value so that the data does not show a significant change from the depth profile of the past feature values.

With reference to the flowchart of FIG. 8, the operation of the ultrasound imaging apparatus of the third embodiment will be described. In the flowchart of FIG. 8, steps S901 to S904 are added between steps S504 and S505 in the flowchart of FIG. 4. There will now be provided descriptions focusing on the steps that are different from FIG. 4.

(Steps S501 to S504)

The receiver 104 receives time-series received signals from the ultrasound transducers, and calculates the depth profiles of the predetermined feature values 1 and 2 obtained from the feature value detector 10.

(Step S901)

The feature value detector 10 stores in the feature value storage memory 25, the depth profile data of the feature values 1 and 2 calculated this time.

(Steps S902 and S903)

The difference calculator 22 reads the depth profiles of the feature values 1 and 2 in the previous time or earlier, from the feature value storage memory 25, and calculates a difference from the depth profiles of the feature values 1 and 2 obtained from the feature value detector 10 this time. The difference calculator 22 determines whether the difference is equal to or greater than a predetermined first threshold. The difference calculator 22 performs processing of step S904 next, when there is found the feature value with the difference equal to or greater than the first threshold being predetermined. When the difference is less than the predetermined first threshold, the process proceeds to step S505.

(Step S904)

The feature value corrector 23 performs correction to bring the present depth profile of the feature value 1 and/or the feature value 2 with the difference equal to or greater than the first threshold, to become closer to the depth profiles of the feature values previous or earlier. For example, an average value is taken between the distribution curve of the depth profile of this time, and the distribution curve of previous time, thereby correcting the depth profile of the feature value of this time with this average value.

(Step S505)

Similar to the type deciders such as 26-1 and 26-2 of the first embodiment, the type decider 26 of the parameter determiner 21 receives the feature values from the feature value detector 10, and determines which of the predetermined types is associated with the feature value, as to each of the feature values.

(Step S506)

Similar to the selectors such as 24-1 and 24-2 of the first embodiment, the selector 24 reads from the parameter value memory 30, values of the parameters associated with the corresponding types, and determines thus read values as the values of the parameters 1 and 2 associated with the feature values 1 and 2 (see FIG. 4).

The aforementioned steps S901 to 904, S505, and S506 are performed for each feature value.

The controller 20 sets the parameter values 1 and 2 determined by the parameter determiner 21 to the signal processor 41 and/or the image processor 42.

(Steps S507 and S508)

In steps S507 and S508, the processing is performed in the same manner as in the first embodiment, and an image is generated. The image processor 42 outputs the generated image to the display device 50 to display the image thereon.

In the ultrasound imaging apparatus of the third embodiment, it is possible to prevent major changes of the depth profiles of the feature values, and thereby reducing significant changes of parameter values between the frames. Therefore, continuity of the image between the frames can be kept and this allows generation of a moving image that facilitates diagnosis.

In the third embodiment, the depth profiles of the feature values are stored in the feature value storage memory 25 to calculate a difference in depth profiles of the feature values between the present time and the previous time and earlier. Alternatively, it is also possible to store the determined parameter value in the memory to calculate a difference between the present parameter value and previous parameter values. Also in this case, it is possible to prevent major changes of the parameter values between frames. Therefore, continuity of the image between the frames can be kept and this allows generation of a moving image that facilitates diagnosis.

Fourth Embodiment

Figure 9:
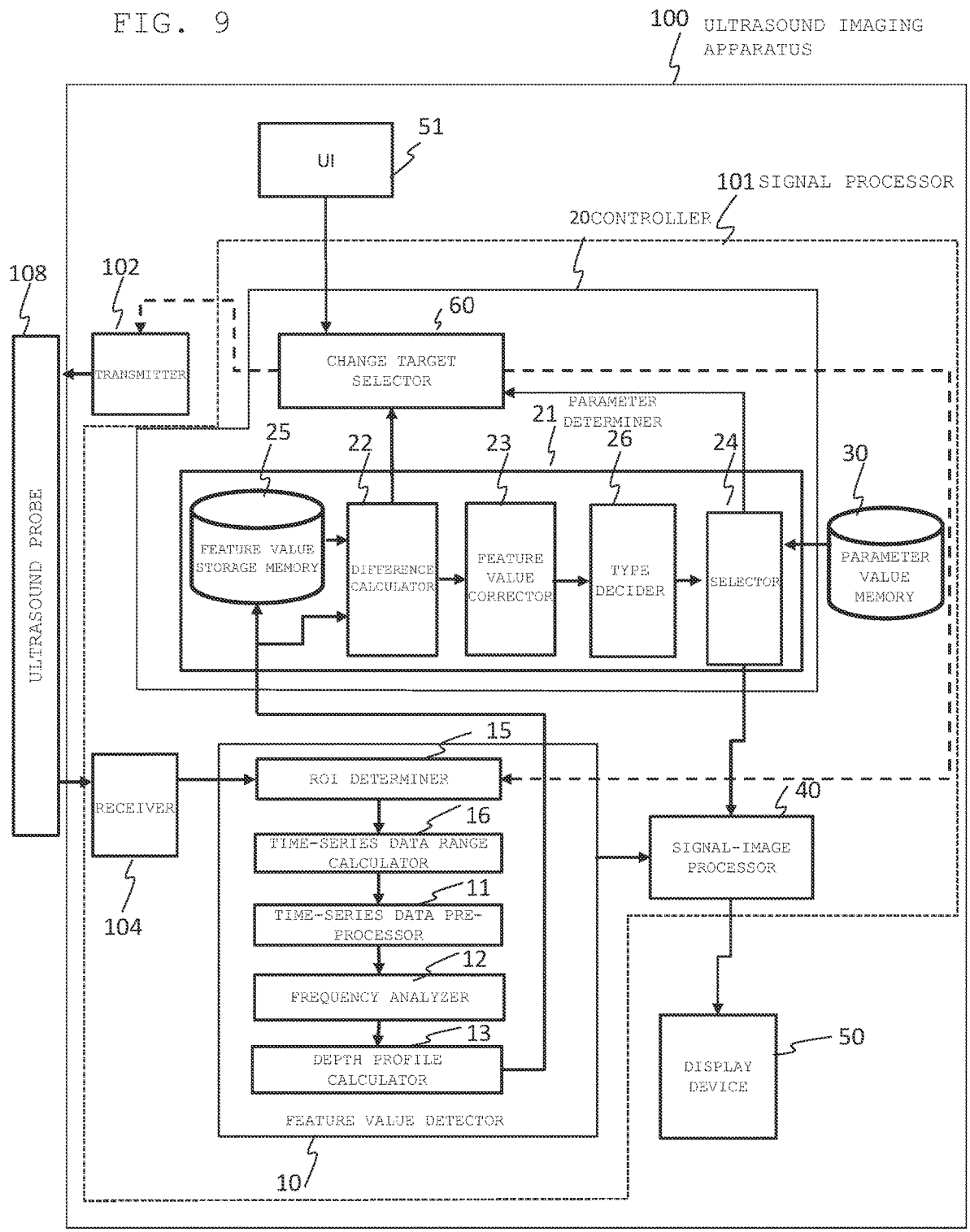
FIG. 9 is a block diagram showing the configuration of the ultrasound imaging apparatus 100 according to a fourth embodiment.
Figure 10:
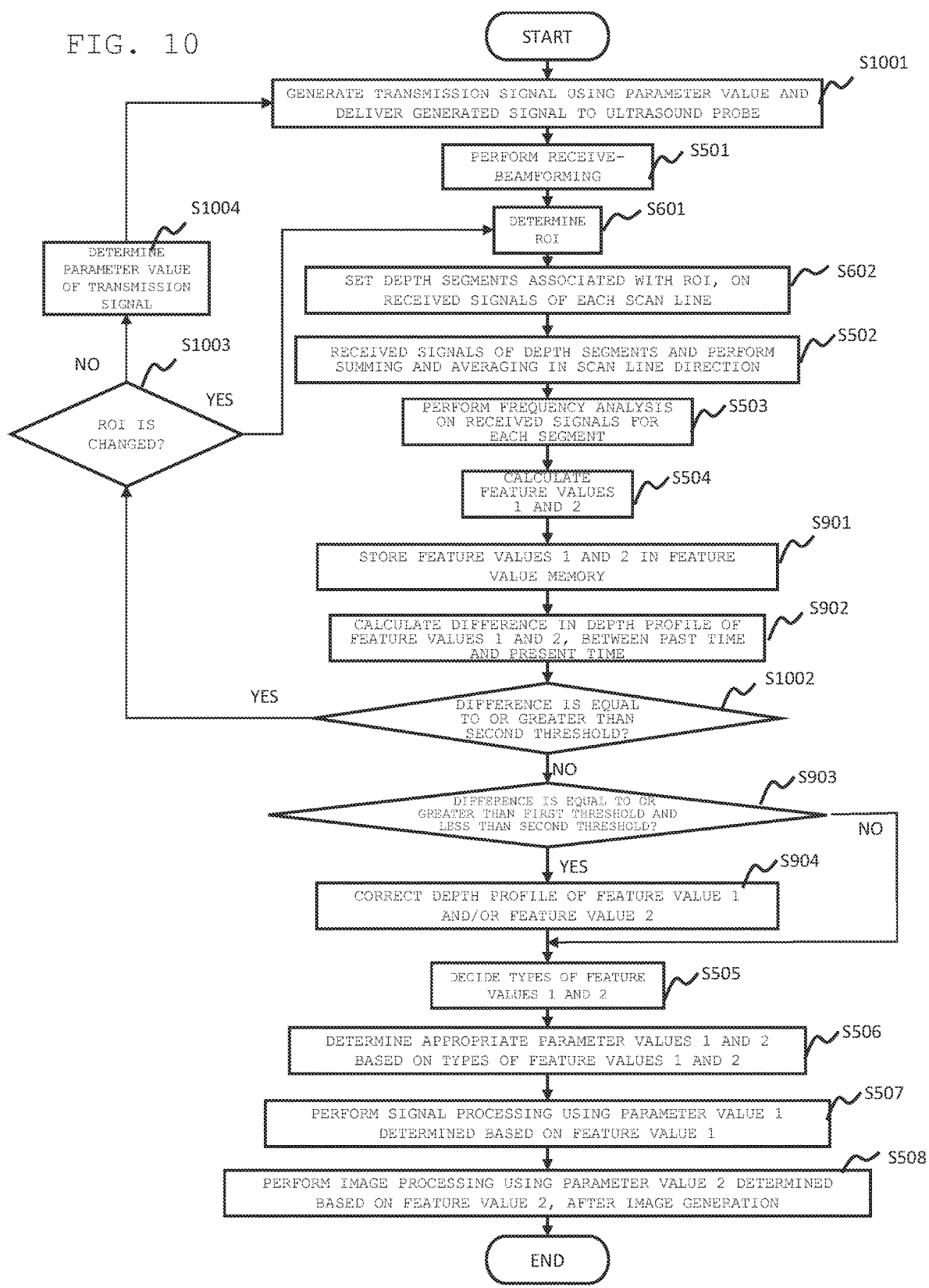
FIG. 10 is a flowchart showing the operation of the ultrasound imaging apparatus 100 according to the fourth embodiment.

With reference to FIGS. 9 and 10, the ultrasound imaging apparatus according to the fourth embodiment of the present invention will be described. FIG. 9 illustrates the configuration of the ultrasound imaging apparatus 100 according to the fourth embodiment, and FIG. 10 is a flowchart showing the operation of this ultrasound imaging apparatus.

The ultrasound imaging apparatus 100 of the fourth embodiment includes the feature value detector 10 in the configuration of the second embodiment, and the parameter determiner 21 in the configuration of the third embodiment. Further, the transmitter 102 of the fourth embodiment generates transmission signals based on one or more parameters and delivers the transmission signals to the ultrasound transducers of the ultrasound probe. Further, the controller 20 includes a change target selector 60.

In the parameter determiner 21, the difference calculator 22 reads the feature values in the previous time or earlier from the feature value storage memory 25 in the same manner as in the third embodiment, and calculates a difference between thus read feature values and the feature values calculated by the feature value detector 10 this time. If the difference is greater than the second threshold determined in advance, the controller 20 changes values of the parameters of the transmitter 102, or the setting area and/or the size of the ROI 17. The change target selector 60 selects whether to change the parameter values of the transmitter 102 or to change ROI 17, based on an instruction or the like, received from the user through the UI 51.

With reference to the flowchart of FIG. 10, there will be described the operation of the ultrasound imaging apparatus according to the third embodiment. In the flowchart of FIG. 10, there are added step S601 and S602 of FIG. 6 according to the second embodiment, between steps S501 and S502 in the flowchart of FIG. 8 according to the third embodiment. Step S1001 for transmission is added prior to step S501 in the flowchart of FIG. 8, and step S1002 for determination is further added between step S902 and step S903. Then, there is also added a loop for returning from step S1002 to step S1001 through steps S1003 and S1004. There will now be described the steps, focusing on the steps different from FIG. 8.

(Step S1001)

The transmitter 102 generates transmission signals using one or more parameters, and delivers the transmission signals to the ultrasound transducers of the ultrasound probe 108. The ultrasound transducers convert the transmission signals into an ultrasound wave, and the subject 120 is irradiated with the ultrasound wave.

(Step S501)

The receiver 104 receives time-series signals from the ultrasound transducers.

(Step S601)

Similar to the second embodiment, the ROI determiner 15 obtains by calculation, a range of one frame image or a range of the image to be generated from the received signals by the signal-image processor 40.

(Step S602)

The ROI determiner 15 sets the ROI 17 within the range of the image. The area for setting the ROI 17 may be a predetermined position (e.g., the center of the image) and size, or the area may be received from the user via the UI 51.

(Steps S502 to S504)

The feature value detector 10 calculates the depth profiles of one or more predetermined feature values, from the received signals that are used to generate the image in the ROI 17.

(Step S901)

The feature value detector stores the depth profile data of the feature values calculated this time in the feature value storage memory 25.

(Step S902)

The difference calculator 22 reads the depth profiles of the feature values in the previous time or earlier, from the feature value storage memory 25, and calculates a difference between thus read depth profiles and those of the feature values calculated this time by the feature value detector 10.

(Step S1002)

When the difference is equal to or greater than the second threshold determined in advance, the feature value is significantly changed from the previous frame, and the processing subsequent to the processing of the difference calculator 22 is step S1003.

(Step S1003)

The change target selector 60 prompts the user to select whether to change the parameter values of the transmitter 102 or to change the ROI 17 in order to respond to the significant change of the feature value, and accepts the user's selection via the UI 51. Other than accepting the selection from the user, the change target selector 60 itself may select either to change the parameter values of the transmitter 102 or to change the ROI 17.

When the change of the ROI 17 is selected, the process of the change target selector 60 returns to step S602, and after changing the position and size of the ROI 17, the process proceeds to step S502 and subsequent steps.

As described above, the change of the position and size of the ROI 17 enables setting of the ROI 17 in the area where the patient-characteristics are shown, and detection of the feature values can be performed once again.

On the other hand, when the change target selector 60 does not select the change of the ROI 17, that is, when the change of the parameter values in the transmitter 102 is selected, the process proceeds to step S1004.

(Step S1004)

In step S1004, the selector 24 selects from the parameter value memory 30, parameter values used for transmission, according the user's selection or automatically, and delivers the parameter values to the change target selector 60. For example, the transmission frequency band is narrowed down and the transmission signals in thus narrowed-down frequency band are transmitted, thereby reducing the noise included in the received signals. In addition, a transmission beam with a transmit-waveform having a lower center-frequency may be transmitted, thereby improving the amplitude of the received signals. This improves the signal-to-noise ratio of the received signals, and enhances the accuracy in detecting features.

The change target selector 60 sets the parameter values to the transmitter 102, and the process returns to the step S1001.

Thus, in the step S1001, the transmitter 102 generates the transmission signals using the parameter values provided from the change target selector 60, and delivers the transmission signals to the ultrasound probe 108 to perform transmission.

This configuration allows switching of the transmission beam to a transmission beam that facilitates showing of the patient characteristics in the received signals, and then the feature values are detected.

(Step S1002)

In the above-described step S1002, when the difference is less than the predetermined second threshold, the process of the difference calculator 22 proceeds to step S903.

(Steps S903 and S904)

The difference calculator 22 determines whether or not the difference calculated in step S902 is equal to or greater than the predetermined first threshold and less than the predetermined second threshold. When the difference calculated in step S902 is equal to or greater than the first threshold and less than the second threshold, the process of the difference calculator 22 proceeds to step S904. Then, similarly to the third embodiment, the depth profiles of the present feature values are corrected to become closer to the depth profiles of the feature values in the previous time or earlier, and the process proceeds to step S505.

When the difference calculated in step S902 is less than the predetermined first threshold, the process of the difference calculator 22 proceeds directly to step S505.

(Steps S505 to S508)

Similar to the first to third embodiments, the parameter determiner 21 determines the parameter values based on the depth profiles of the feature values calculated by the feature value detector 10. Using the parameter values, the signal processor 41 generates an image and the image processor 42 performs image processing. The image processor 42 delivers the generated image to the display device 50 and displays the image.

When there is an extremely large change in the depth profiles of the feature values, the ultrasound imaging apparatus of the fourth embodiment changes the transmission parameters and switches the transmission beam. Alternatively, by changing the position and size of the ROI 17, the characteristics of the subject can be easily shown in the depth profiles of the feature values. Therefore, this increases accuracy in detecting the feature values of the subject, enabling the feature value detection with improved robustness, as well as stable detection of depth profiles.

Fifth Embodiment

Figure 11:
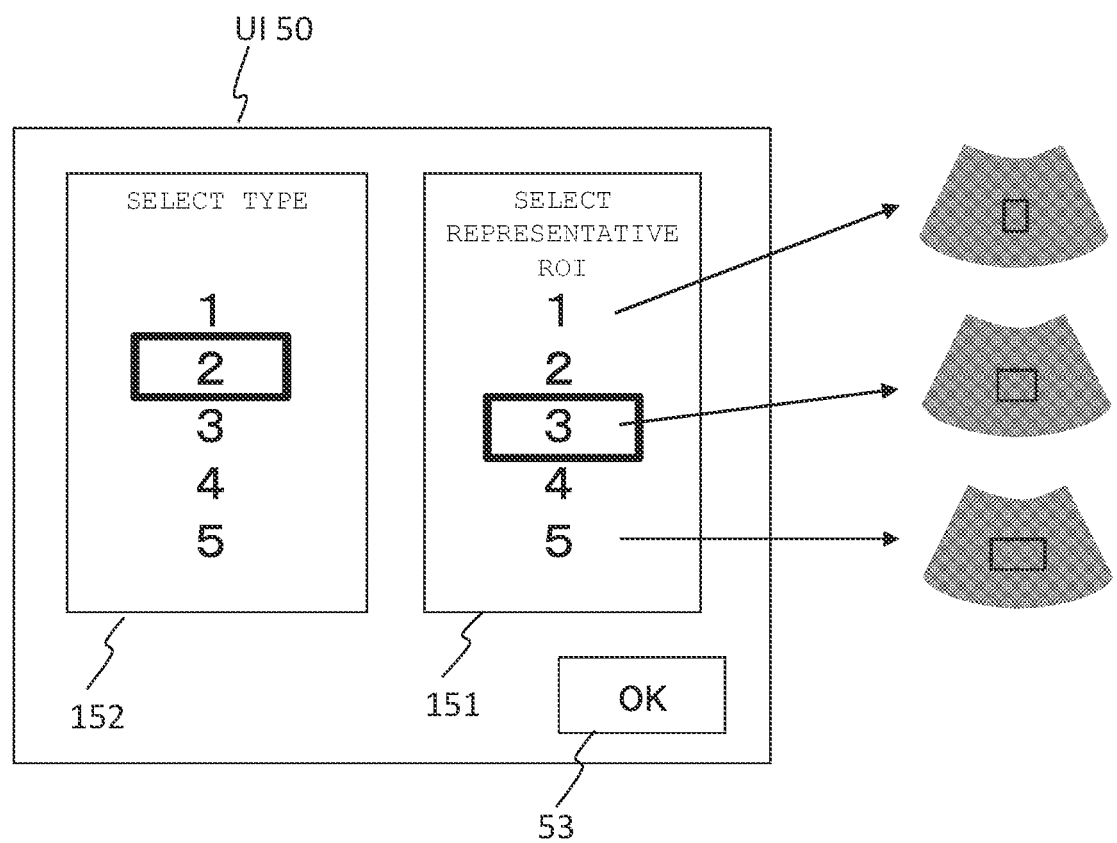
FIG. 11 illustrates an example of a screen for accepting selection of ROI from a user according to a fifth embodiment.

There will be described the fifth embodiment with reference to FIG. 11, as an example of a screen displayed on the display device 50. The screen shown in FIG. 11 is an example of the screen displayed on the display device 50 for the ROI-determiner 15 to determine the ROI 17 in step S601 of the second embodiment and the fourth embodiment. A user performs operations on the screen of FIG. 11, thereby allowing the ROI determiner 15 to select the feature value type and the position of the representative ROI.

A type as a result of determination based on the received signals during the imaging is displayed on the type selection screen 152, and the user checks the ultrasound image against the result of type determination, thereby deciding the appropriateness of the parameters being applied based on the determination result. In order to depict the ultrasound image more suitable for diagnostic purposes, the user moves the cursor on the type selection screen 152, so as to view the image with the parameters that are applied according to a different determined type. In addition, the user moves the cursor on the ROI selection screen 151 and presses the OK button 53, so as to select a representative ROI in a representative area where patient characteristics are shown. In addition to the method of selecting one of the predetermined correspondences between the number and the ROI size, as in the example of FIG. 11, there is also a method of manually surrounding the area, using an operation panel.

What is claimed is:

1. An ultrasound imaging apparatus comprising:
   a receiver configured to receive signals outputted in time series from a plurality of ultrasound transducers that have received an ultrasound wave from a subject irradiated with the ultrasound wave;
   a feature value detector configured to calculate from the received signals, a feature value indicating a frequency-dependent characteristic of attenuation of the ultrasound wave, associated with propagation of the ultrasound wave through the subject;
   a signal-image processor configured to execute a predetermined process on the received signals, using one or more received-signal processing parameters to generate an image, and to perform an image processing on thus generated image, using one or more image processing parameters; and
   a controller configured to set values of the received-signal processing parameter and the image processing parameter used by the signal-image processor, to execute processing,
   wherein the controller comprises a parameter determiner that determines a value or values of one or more parameters among the received-signal processing parameters and the image processing parameters, on the basis of the feature value calculated by the feature value detector, the parameter determiner comprising
      a feature value storage memory configured to store the feature value,
      a difference calculator configured to read the feature value of a previous time or earlier from the feature value storage memory and to calculate a difference between the read feature value and the feature value calculated by the feature value detector this time,
      a feature value corrector configured to correct the feature value of this time, when the difference is greater than a predefined first threshold, and
      a selector configured to select a corresponding parameter value from predetermined parameter values, using the feature value corrected by the feature value corrector.

2. The ultrasound imaging apparatus according to claim 1, wherein
   the controller sets the parameter values determined by the parameter determiner, when common received signals are processed by the signal-image processor, thereby allowing the feature value to be reflected in real time on generation of the image according to the signal-image processor.

3. The ultrasound imaging apparatus according to claim 1, wherein
   the feature value detector obtains information of a frequency component that varies in a depth direction of the received signals, and calculates the feature value based on the information.

4. The ultrasound imaging apparatus according to claim 3, wherein the feature value detector comprises
   a pre-processor configured to divide the received signals into a plurality of depth segments, and to extract the received signals in the plurality of depth segments,
   a frequency analyzer configured to perform frequency analysis on the received signals in each of the plurality of depth segments, extracted by the pre-processor, and a depth profile calculator configured to obtain from information indicated by the frequency components of the received signals in the plurality of segments, having been analyzed by the frequency analyzer, a change in the depth direction of a characteristic indicated by a predetermined frequency component, and outputs the change as the feature value.

5. The ultrasound imaging apparatus according to claim 3, wherein
the receiver applies beamforming to the received signals outputted from the plurality of ultrasound transducers along a predetermined scan line, and
the feature value detector performs processing on the received signals after beamforming to obtain the feature value.

6. The ultrasound imaging apparatus according to claim 3, wherein
the feature value detector calculates as the feature value, at least one of the followings; a change in the depth direction of center frequency of the received signals, a change in the depth direction of a transmission band of the received signals, a change in the depth direction of maximum amplitude within a predetermined frequency section, and a change in the depth direction of either of power and energy.

7. The ultrasound imaging apparatus according to claim 1, wherein
the ultrasound wave applied to the subject are irradiated in the depth direction of the subject, and
the received-signal processing parameter includes a parameter to change one or more values of a depth-varying bandpass filter, a depth-varying receive aperture, and a depth-varying sound speed, used in processing the received signals.

8. The ultrasound imaging apparatus according to claim 1, wherein
the ultrasound wave is applied to the subject are irradiated in the depth direction of the subject, and
the image processing parameter is a parameter for changing a value of time gain control.

9. The ultrasound imaging apparatus according to claim 1, further comprising a transmitter, wherein
the transmitter generates transmission signals based on one or more parameters, delivers the transmission signals to the ultrasound transducers, and allows the ultrasound transducers to convert the transmission signals to an ultrasound wave to be applied to the subject, and
the parameter determiner sets a value of one or more parameters among the parameters used for generating the transmission signals by the transmitter, based on the feature value.

10. An ultrasound imaging apparatus comprising:
a receiver configured to receive signals outputted in time series from a plurality of ultrasound transducers that have received an ultrasound wave from a subject irradiated with the ultrasound wave;
a feature value detector configured to calculate from the received signals, a feature value indicating a frequency-dependent characteristic of attenuation of the ultrasound wave, associated with propagation of the ultrasound wave through the subject;
a signal-image processor configured to execute a predetermined process on the received signals, using one or more received-signal processing parameters to generate an image, and to perform an image processing on thus generated image, using one or more image processing parameters; and
a controller configured to set values of the received-signal processing parameter and the image processing parameter used by the signal-image processor, to execute processing,
wherein the controller comprises a parameter determiner that determines a value or values of one or more parameters among the received-signal processing parameters and the image processing parameters, on the basis of the feature value calculated by the feature value detector,
wherein the feature value detector obtains information of a frequency component that varies in a depth direction of the received signals, and calculates the feature value based on the information,
wherein the feature value detector comprises
a pre-processor configured to divide the received signals into a plurality of depth segments, and to extract the received signals in the plurality of depth segments,
a frequency analyzer configured to perform frequency analysis on the received signals in each of the plurality of depth segments, extracted by the pre-processor, and
a depth profile calculator configured to obtain from information indicated by the frequency components of the received signals in the plurality of segments, having been analyzed by the frequency analyzer, a change in the depth direction of a characteristic indicated by a predetermined frequency component, and outputs the change as the feature value, and
wherein the ultrasound imaging apparatus further comprises a parameter value memory, wherein in the parameter value memory, a plurality of predetermined types according to ways of change of the feature value in the depth direction, and predetermined parameter values for each of the plurality of predetermined types are stored in association with each other, and
wherein the parameter determiner comprises
a type decider configured to decide which of the plurality of types corresponds to the change in the depth direction of the feature value obtained by the feature value detector for the received signals, and
a selector configured to select the parameter value corresponding to thus decided type, from the parameter value memory.

11. The ultrasound imaging apparatus according to claim 2, wherein
the controller allows the feature value detector and the signal-image processor to perform each processing according to pipeline processing, the processing by the feature value detector being performed on a preceding stage of the processing of the signal-image processor, and the controller sets the parameter values obtained from the feature value, as the parameter values used in the signal-image processor on a subsequent stage.

12. An ultrasound imaging apparatus comprising:
a receiver configured to receive signals outputted in time series from a plurality of ultrasound transducers that have received an ultrasound wave from a subject irradiated with the ultrasound wave;
a feature value detector configured to calculate from the received signals, a feature value indicating a frequency-dependent characteristic of attenuation of the ultrasound wave, associated with propagation of the ultrasound wave through the subject;

a signal-image processor configured to execute a predetermined process on the received signals, using one or more received-signal processing parameters to generate an image, and to perform an image processing on thus generated image, using one or more image processing parameters; and a controller configured to set values of the received-signal processing parameter and the image processing parameter used by the signal-image processor, to execute processing, wherein the controller comprises a parameter determiner that determines a value or values of one or more parameters among the received-signal processing parameters and the image processing parameters, on the basis of the feature value calculated by the feature value detector, wherein the feature value detector obtains information of a frequency component that varies in a depth direction of the received signals, and calculates the feature value based on the information, wherein the feature value detector comprises
a pre-processor configured to divide the received signals into a plurality of depth segments, and to extract the received signals in the plurality of depth segments,
a frequency analyzer configured to perform frequency analysis on the received signals in each of the plurality of depth segments, extracted by the pre-processor,
a depth profile calculator configured to obtain from information indicated by the frequency components of the received signals in the plurality of segments, having been analyzed by the frequency analyzer, a change in the depth direction of a characteristic indicated by a predetermined frequency component, and outputs the change as the feature value, and
an ROI determiner configured to set a plurality of ROIs in the depth direction within a range of the image generated from the received signals, and
a range calculator configured to extract the received signals of the plurality of scan lines used for generating the images within the plurality of ROIs, and sets depth segments on the depths respectively associated with the depth ranges of the ROIs for the extracted received signals, and wherein the pre-processor sums and averages the received signals in the depth segments within the same ROI after the extraction of the received signals in the depth segments set by the range calculator, the frequency analyzer performs frequency analysis on the received signals after the summing and averaging, and the depth profile calculator calculates the feature value of the ROI based on a result of the frequency analysis of the received signals after the summing and averaging.

13. The ultrasound imaging apparatus according to claim 12, wherein the parameter determiner comprises
a feature value storage memory configured to store the feature value,
a difference calculator configured to read the feature value of a previous time or earlier from the feature value storage memory and to calculate a difference between the read feature value and the feature value calculated by the feature value detector this time, and
wherein when the difference is greater than the predefined second threshold, the ROI determiner changes a setting area and/or size of the ROI.

14. An ultrasound imaging apparatus comprising:
a receiver configured to receive signals outputted in time series from a plurality of ultrasound transducers that have received an ultrasound wave from a subject irradiated with the ultrasound wave;
a feature value detector configured to calculate from the received signals, a feature value indicating a frequency-dependent characteristic of attenuation of the ultrasound wave, associated with propagation of the ultrasound wave through the subject;
a signal-image processor configured to execute a predetermined process on the received signals, using one or more received-signal processing parameters to generate an image, and to perform an image processing on thus generated image, using one or more image processing parameters;
a controller configured to set values of the received-signal processing parameter and the image processing parameter used by the signal-image processor, to execute processing, wherein the controller comprises a parameter determiner that determines a value or values of one or more parameters among the received-signal processing parameters and the image processing parameters, on the basis of the feature value calculated by the feature value detector; and
a transmitter, wherein the transmitter generates transmission signals based on one or more parameters, delivers the transmission signals to the ultrasound transducers, and allows the ultrasound transducers to convert the transmission signals to an ultrasound wave to be applied to the subject, and
wherein the parameter determiner comprises
a feature value storage memory configured to store the feature value,
a difference calculator configured to read the feature value of a previous time or earlier from the feature value storage memory and to calculate a difference between the read feature value and the feature value calculated by the feature value detector this time, and
a selector configured to select a parameter value of the transmitter, from predetermined parameter values, when the difference is greater than a predefined second threshold.

\* \* \* \* \*